(12) United States Patent
Faqihi et al.

(10) Patent No.: US 9,933,327 B2
(45) Date of Patent: Apr. 3, 2018

(54) METHOD FOR DETECTING LEAKS IN A FUEL CIRCUIT OF A GAS TURBINE FUEL SUPPLY SYSTEM

(71) Applicant: General Electric Company, Schenectady, NY (US)

(72) Inventors: Bouria Faqihi, Dubai (AE); Abdul Khaliq, Manama (BH); James Frederik den Outer, Simpsonville, SC (US); Thomas Earnest Moldenhauer, Burnt Hills, NY (US); Michael Lynch, Atlanta, GA (US); Richard Preston Epley, Clemson, SC (US); Steven Castellaw, Greenville, SC (US); Sheng Jia Zheng, Simpsonville, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 133 days.

(21) Appl. No.: 14/967,654

(22) Filed: Dec. 14, 2015

(65) Prior Publication Data

US 2017/0052087 A1    Feb. 23, 2017

Related U.S. Application Data

(60) Provisional application No. 62/207,639, filed on Aug. 20, 2015.

(51) Int. Cl.
*G01M 3/24* (2006.01)
*G01M 3/02* (2006.01)
(Continued)

(52) U.S. Cl.
CPC ............ *G01M 3/243* (2013.01); *G01M 3/025* (2013.01); *F01D 19/00* (2013.01); *F01D 21/14* (2013.01);
(Continued)

(58) Field of Classification Search
CPC ......... G01M 3/243; G01M 3/007; F02C 7/22; F02C 9/263; G01N 29/14; F02K 9/54
(Continued)

(56) References Cited

U.S. PATENT DOCUMENTS 3,992,924 A   11/1976   Ells et al.
4,096,736 A   6/1978    Moshier
(Continued)

FOREIGN PATENT DOCUMENTS

EP    0359570 A2    3/1990
EP    0359570 A3    3/1990
(Continued)

OTHER PUBLICATIONS

Generant Valves and fittings, Adjustable Check Valve, Wayback Machine Snapshot, Dec. 7, 2013.*

*Primary Examiner* — Manish S Shah
*Assistant Examiner* — Timothy Graves
(74) *Attorney, Agent, or Firm* — Dority & Manning, P.A.

(57) ABSTRACT

A method for detecting leakage at a fluid connection for a gas turbine fuel supply system is disclosed herein. The method includes closing a flow control valve at an upstream end of the fuel supply system and pressurizing the fuel supply system with a compressed medium via a compressed medium supply to a target pressure. The target pressure is less than a pressure threshold of a check valve that is disposed downstream from the compressed medium supply and upstream from a corresponding combustor of the gas turbine. The method further includes pointing a receiver portion of an ultrasonic detection device proximate to at least one tube fitting of the fuel supply system located between the flow control valve and a combustor which is fluidly coupled to the fuel supply system. Detection of an
(Continued)

increase in sound level and/or the sound of popping at the tube fitting is indicative of a leak at the tube fitting.

13 Claims, 3 Drawing Sheets

(51) Int. Cl.
  *F01D 25/00* (2006.01)
  *F01D 19/00* (2006.01)
  *F02C 9/46* (2006.01)
  *G01M 3/26* (2006.01)
  *F02C 7/22* (2006.01)
  *F02C 9/28* (2006.01)
  *F01D 21/14* (2006.01)
  *F02C 7/00* (2006.01)
  *F02C 9/26* (2006.01)
  *G01M 3/00* (2006.01)
  *G01N 29/14* (2006.01)
  *F02K 9/54* (2006.01)

(52) U.S. Cl.
  CPC ............... *F01D 25/00* (2013.01); *F02C 7/00* (2013.01); *F02C 7/22* (2013.01); *F02C 9/263* (2013.01); *F02C 9/28* (2013.01); *F02C 9/46* (2013.01); *F02K 9/54* (2013.01); *F05D 2260/80* (2013.01); *G01M 3/007* (2013.01); *G01M 3/26* (2013.01); *G01N 29/14* (2013.01)

(58) Field of Classification Search
  USPC ...................................................... 73/40.5 A
  See application file for complete search history.

(56) References Cited

U.S. PATENT DOCUMENTS

| | | | |
|---|---|---|---|
| 4,096,738 A | 6/1978 | Rupp et al. | |
| 4,172,379 A | 10/1979 | van Tilburg et al. | |
| 4,196,631 A | 4/1980 | Déom et al. | |
| 4,365,514 A | 12/1982 | Ho | |
| 4,485,739 A * | 12/1984 | Emmett | F42D 1/10 102/200 |
| 4,809,538 A | 3/1989 | Fisch | |
| 4,987,769 A | 1/1991 | Peacock et al. | |
| 5,016,475 A | 5/1991 | Aburatani et al. | |
| RE33,977 E * | 6/1992 | Goodman | G01M 3/24 73/40.5 A |
| 5,400,645 A | 3/1995 | Kunze et al. | |
| 5,408,867 A | 4/1995 | Kunze et al. | |
| 5,433,104 A | 7/1995 | Kunze et al. | |
| 5,710,377 A * | 1/1998 | Youngquist | G01H 3/00 73/40.5 A |
| 5,854,422 A | 12/1998 | McKeon et al. | |
| 5,955,670 A | 9/1999 | Goodman et al. | |
| 5,979,239 A | 11/1999 | Youngquist et al. | |
| 6,070,468 A | 6/2000 | Degertekin et al. | |
| 6,189,384 B1 | 2/2001 | Piety et al. | |
| 6,430,988 B1 | 8/2002 | Watanabe | |
| 6,588,278 B1 | 7/2003 | Takishita et al. | |
| 7,054,055 B2 | 5/2006 | Shibuya et al. | |
| 7,213,630 B2 | 5/2007 | Kendall et al. | |
| 7,289,918 B2 | 10/2007 | Nagase | |
| 7,318,335 B2 | 1/2008 | Olesen et al. | |
| 7,387,026 B1 | 6/2008 | Gayle | |
| 7,479,169 B2 | 1/2009 | Yagi et al. | |
| 7,711,500 B1 | 5/2010 | Killion et al. | |
| 7,739,899 B1 | 6/2010 | Holland et al. | |
| 7,817,050 B2 | 10/2010 | Goodman et al. | |
| 7,890,276 B2 | 2/2011 | Killion et al. | |
| 7,987,720 B2 | 8/2011 | Gayle | |
| 8,365,580 B2 | 2/2013 | Stumpf | |
| 8,542,124 B2 | 9/2013 | Timm | |
| 8,955,383 B2 | 2/2015 | Huseynov et al. | |
| 9,091,613 B2 | 7/2015 | Baliga | |
| 2002/0112527 A1 | 8/2002 | Nadin | |
| 2002/0120411 A1 * | 8/2002 | Fierro | G01M 3/2815 702/51 |
| 2005/0069644 A1 | 3/2005 | Hsieh et al. | |
| 2009/0007968 A1 | 1/2009 | Knecht et al. | |
| 2009/0210175 A1 | 8/2009 | Bilpuch | |
| 2010/0154515 A1 | 6/2010 | Killion et al. | |
| 2010/0307225 A1 | 12/2010 | Yoshida | |
| 2012/0247189 A1 | 10/2012 | Finlay | |
| 2013/0239662 A1 * | 9/2013 | Penza | G01M 3/2815 73/40.5 R |

FOREIGN PATENT DOCUMENTS

| | | |
|---|---|---|
| EP | 1371962 A1 | 12/2003 |
| EP | 1522839 A1 | 4/2009 |
| WO | WO 94/21996 A1 | 9/1994 |
| WO | WO2005/031206 A1 | 4/2005 |
| WO | WO2005/036120 A1 | 4/2005 |

* cited by examiner

METHOD FOR DETECTING LEAKS IN A FUEL CIRCUIT OF A GAS TURBINE FUEL SUPPLY SYSTEM

CROSS REFERENCE TO RELATED APPLICATIONS

The present application claims filing benefit of U.S. Provisional Patent Application Ser. No. 62/207,639 having a filing date of Aug. 20, 2015, which is incorporated by reference herein in its entirety.

FIELD OF THE INVENTION

The present disclosure relates to a method for detecting leaks in a fuel circuit of a gas turbine fuel supply system.

BACKGROUND OF THE INVENTION

A gas turbine generally includes, in serial flow order, a compressor section, a combustion section and a turbine section. During operation, air enters the compressor via an inlet system and is progressively compressed as it is routed towards a compressor discharge or diffuser casing. The compressed air is routed into individual combustors of the combustion section. At least a portion of the compressed air is mixed with a fuel and burned within a corresponding combustion chamber defined within each combustor, thereby generating high temperature and high pressure combustion gases.

Liquid fuel may be supplied to the combustors from a fuel supply skid or system via various pipes, conduits, valves and tube fittings. During installation and/or over time, fuel leaks may be present or develop around the fittings. One known method for detecting fuel leaks is to pressurize the fuel circuit with the fuel or an inert gas such as nitrogen at a full working pressure which is typically from about 500 psig or greater. Although effective, this leak detection process has a few drawbacks. For example, one drawback is that the current process is time intensive. More specifically, in order to complete this detection process the tubes routed to each combustor or combustion can has to be disconnected upstream from a corresponding check valve or 3-way valve and tested separately before being reconnected. The primary reason for this is that the check or 3-way valves are configured to open at about 100 psig. As a result, if the tubes were connected the fuel circuit would depressurize when the pressure exceed 100 psig, thereby causing a loss of test pressure. This may also mean that the final connection at the check or 3-way vales cannot be verified in the test. In addition, testing at 500 psig and above, especially with compressible fluid, may require special safety considerations for technicians.

Accordingly, there is a need to provide an improved method or process for detecting leaks in a fuel circuit of a gas turbine. More particularly, there is a need to provide a method for detecting fuel system fitting or fluid coupling leaks for a gas turbine combustor with the ability to leave the corresponding tubes or conduits in situ.

BRIEF DESCRIPTION OF THE INVENTION

Aspects and advantages of the invention are set forth below in the following description, or may be obvious from the description, or may be learned through practice of the invention.

One embodiment of the present invention is a method for detecting leakage at a fluid connection for a gas turbine fuel supply system. The method includes closing a flow control valve at an upstream end of the fuel supply system and pressurizing the fuel supply system with a compressed medium via a compressed medium supply to a target pressure. The target pressure is less than a pressure threshold of a check valve that is disposed downstream from the compressed medium supply and upstream from a corresponding combustor of the gas turbine. The method further includes pointing a receiver portion of an ultrasonic detection device proximate to at least one tube fitting of the fuel supply system located between the flow control valve and a combustor which is fluidly coupled to the fuel supply system. Detection of an increase in sound level or the sound of bubbles popping at the tube fitting is indicative of a leak at the tube fitting.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
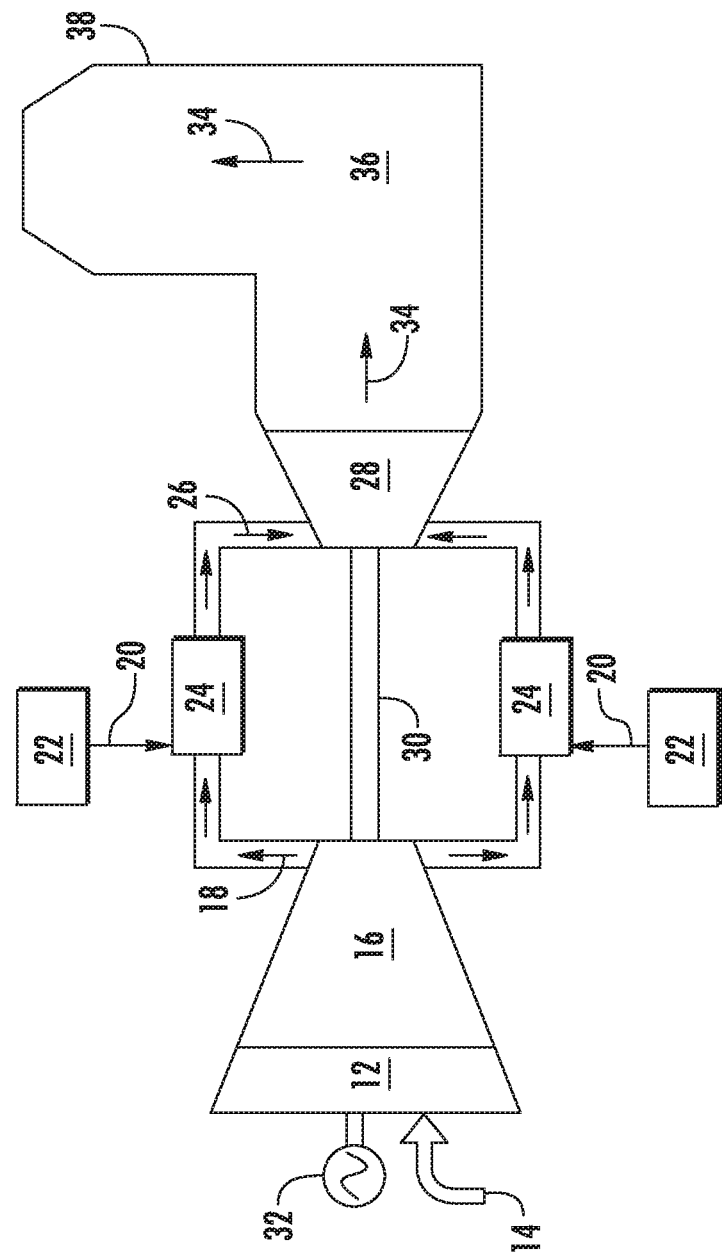
FIG. 1 is a functional block diagram of an exemplary gas turbine based power plant within the scope of the present invention.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. As used herein, the terms "first", "second", and "third" may be used interchangeably to distinguish one component from another and are not intended to signify location or importance of the individual components. The terms "upstream" and "downstream" refer to the relative direction with respect to fluid flow in a fluid pathway. For example, "upstream" refers to the direction from which the fluid flows, and "downstream" refers to the direction to which the fluid flows. The term "radially" refers to the relative direction that is substantially perpendicular to an axial centerline of a particular component, and the term "axially" refers to the relative direction that is substantially parallel and/or coaxially aligned to an axial centerline of a particular component.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

An embodiment of the present invention takes the form of a method for detecting fuel fitting leaks for a fuel supply circuit of a gas turbine. The method includes pressurizing the fuel circuit to be tested to between about 50 psig to about 80 psig using air or an inert pressurized gas such as nitrogen. The method then includes using an ultrasonic device to detect leakages at various tube fittings and/or fluid couplings or connections. Leakages detected at such pressures may be equivalent to about 60 drops per minute at a full working pressure of liquid fuel at 500 psig. The leak detection method resolves two problems that may occur with currently known leak detection processes. First, there is no need to disconnect any connections along the fuel circuits because the test pressure remains under check valve cracking pressure of about 100 psig for particular combustors. Second, a fuel circuit pressure in the range of about 50 psig to about 80 psig may reduce potential hazards associated with testing at full operating pressures of about 500 psig.

The ultrasonic device is generally engineered to detect the ultrasonic noise generated by the turbulence created by a leak at the fittings. One reason that this method is successful is that ultrasound is directional and thus detectable by the ultrasonic device, thus allowing the operator to quickly find the source of the noise. With known processes, every individual fitting connection, and there are many hundreds of connections, must by sprayed with a leak detection liquid such as "Snoop" and then visually inspected for bubbles. With the method provided herein, the ultrasonic detection device may find large leaks immediately and only suspect fittings with very small leaks may require follow-up with the Liquid Leak Amplifier. In addition, the method as provided herein does not require the application of the Snoop on very hard to reach connections such as connections where the leak is 180-degrees away from the Snoop operator.

Referring now to the drawings, wherein identical numerals indicate the same elements throughout the figures, FIG. 1 provides a functional block diagram of an exemplary power plant site comprising a gas turbine 10 that may incorporate various embodiments of the present invention. As shown, the gas turbine 10 may generally include an inlet section 12. The inlet section 12 may include a series of filters, cooling coils, moisture separators, and/or other devices to purify and otherwise condition air 14 or other working fluid entering the gas turbine 10. The air 14 flows to a compressor section where a compressor 16 progressively imparts kinetic energy to the air 14 to produce compressed air 18.

The compressed air 18 is mixed with a fuel 20 such as a liquid from a fuel supply system 22 to form a combustible mixture within one or more combustors 24. The combustible mixture is burned to produce combustion gases 26 having a high temperature, pressure and velocity. The combustion gases 26 flow through a turbine 28 of a turbine section to produce work. For example, the turbine 28 may be connected to a shaft 30 so that rotation of the turbine 28 drives the compressor 16 to produce the compressed air 18. Alternately or in addition, the shaft 30 may connect the turbine 28 to a generator 32 for producing electricity. Exhaust gases 34 from the turbine 28 flow through an exhaust section 36 that connects the turbine 28 to an exhaust stack 38 downstream from the turbine 28. The exhaust section 36 may include, for example, a heat recovery steam generator (not shown) for cleaning and extracting additional heat from the exhaust gases 34 prior to release to the environment.

Figure 2:
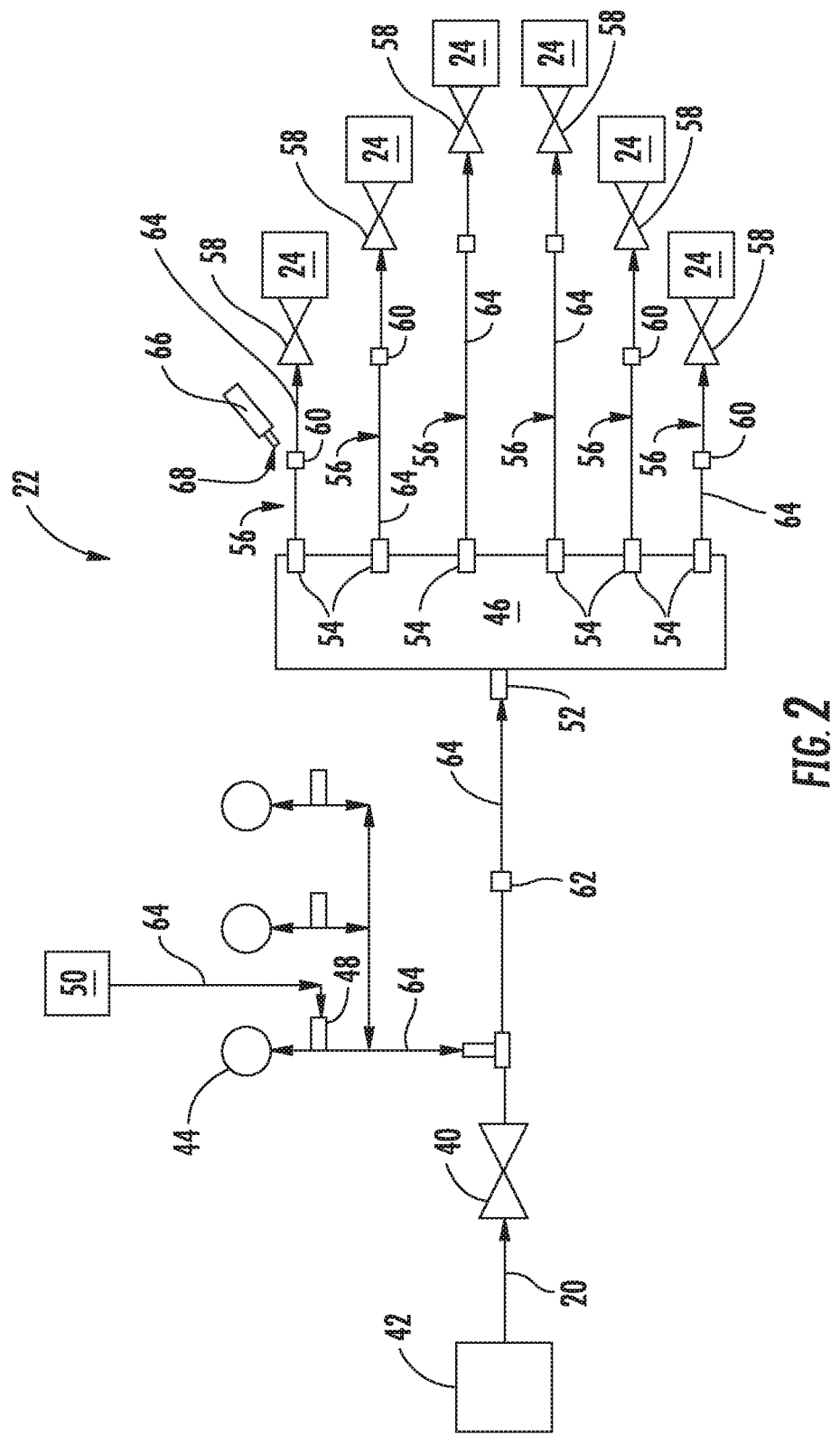
FIG. 2 is a simplified cross sectioned side view of an exemplary fuel supply system as may be incorporated into at least one embodiment of the present invention.

FIG. 2 provides a simplified schematic of an exemplary fuel supply system 22 as may be incorporated into the gas turbine 10 illustrated in FIG. 1. As shown in FIG. 2, the fuel supply system 22 generally includes at least flow control or stop valve 40 or other actuating type valve that is in fluid communication with a liquid fuel source 42. At least one pressure sensor 44 such as a pressure transmitter or gauge is disposed downstream from the flow control valve 40 and upstream from a fuel distribution manifold or splitter 46. A vent or inlet port 48 is positioned between the pressure sensor 44 and the fuel distribution manifold 46. In one embodiment, the inlet port 48 may be disposed downstream from the fuel distribution manifold 46. In particular embodiments, the inlet port 48 is coupled to a compressed medium supply 50. In particular embodiments, the compressed medium supply 50 may comprise an air supply such as an instrumentation air supply. In other embodiments, the compressed medium supply may comprise a pressurized fluid source.

In various embodiments, the fuel distribution manifold 46 includes an inlet 52 in fluid communication with the flow control valve 40 and/or the liquid fuel source 42 and a plurality of outlets 54 disposed downstream from the inlet 52. Each outlet 54 feeds a corresponding fuel circuit 56. Each fuel circuit 56 fluidly couples the fuel distribution manifold 46 to a corresponding combustor 24. Although six outlets 54, six fuel circuits 56 and six combustors 24 are shown for illustration purposes, it should be understood that the fuel distribution manifold 46 may include any number of outlets depending on the number of combustors 24 of a particular gas turbine frame and the present disclosure is not limited to six outlets 54, six fuel circuit 56 or six combustors 24 unless otherwise provided in the claims.

Each fuel circuit 56 includes a corresponding check valve 58 that provides for fluid communication between the corresponding outlet 54 and the corresponding combustor 24. In particular embodiments, the check valve 58 is configured to remain closed at pressures within the fuel circuit 54 of less than about 100 psig, thereby preventing fuel flow to the corresponding combustor 24. The check valve(s) 58 are configured to open at pressures that exceed about 100 psig, thus allowing fuel flow to the corresponding combustor 24. In particular embodiments, the check valve 58 may be a two-way valve, a three-way valve, a four-way valve or may be any type of valve that controls flow based on pressure within the fluid circuit.

Each of the liquid fuel supply 42, the flow control valve 40, the pressure sensor(s) 44, the inlet port(s) 48, the fuel distribution manifold 46, the check valves 58 and the combustors 24 are fluidly coupled via various fluid conduits, pipes, tubes and tube fittings. In various embodiments, a plurality of tube fittings 60 is disposed upstream from each check valve 58 and downstream from the flow control valve 40. In particular embodiments, at least one tube fitting 62 may be disposed downstream from the flow control valve 40 and upstream from the fuel distribution manifold 46.

During fired operation of the gas turbine 10, fuel 20 flows from the liquid fuel supply 42 through the flow control valve 40 and into the fuel distribution manifold 46. The fuel 20 is then routed through the plurality of outlets 54 into the various corresponding fuel circuits 56. Once the pressure within a particular fuel circuit 56 exceeds a predefined threshold pressure such as 100 psig, the corresponding check valve(s) 58 open(s) automatically, thus allowing for the fuel 20 to flow into the corresponding combustor 24. The pressure sensor(s) 44 provide a pressure reading that is representative of fuel pressure within the fuel supply system 22 between the flow control valve 40 and the combustor 24 when the check valve 58 is open such as when the pressure exceeds a predefined pressure threshold. The pressure sensor(s) 44 provide a pressure reading that is representative of fuel pressure within the fuel supply system 22 between the flow control valve 40 and the check valve(s) 58 when the check valve(s) 58 is/are closed such as when the pressure is below the predefined threshold pressure.

Figure 3:
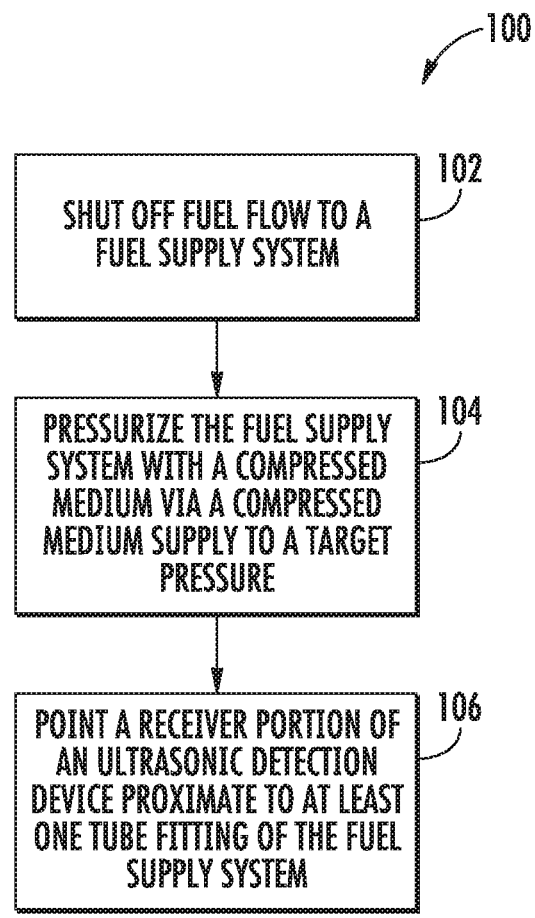
FIG. 3 provides a flow diagram of a method for detecting fuel leakage at tube fittings and/or other fluid couplings or connections of the fuel supply system according to one embodiment of the present disclosure.

During installation and/or over time, fuel leaks may develop at the various tube fittings 60 positioned between the flow control valve 40 and the check valves 58. As such, a method 100 for detecting leakage at the tube fittings 60 and/or other fluid couplings or connections is provided herein. FIG. 3 provides a flow diagram of the method 100 according to one embodiment of the present invention.

At step 102, method 100 includes shutting off fuel flow to the fuel supply system 22 via the flow control valve 40. By closing the flow control valve 40, fuel flow from the liquid fuel supply 42 is shut off. Prior to or after the flow control valve 40 is closed, the fuel supply system 22 may be purged via a purge medium such as air to clear any residual liquid fuel, particularly downstream from the flow control valve 40.

At step 104, method 100 includes pressurizing the fuel supply system 22 with a compressed medium 64 such as air via the compressed medium supply 50. The fuel supply system 22 should be pressurized at a target pressure that is less than a predefined threshold pressure for the check valve 58 such that the check valve does not crack or open. As a result, the pressure sensor 44 will provide a pressure reading that represents a pressure between the flow control valve 40 and the check valve 58. In one embodiment, the threshold pressure is within a range of about 100 psig to about 130 psig. In one embodiment, the threshold pressure is 100 psig. In one embodiment, the target pressure is within a range of about 40 psig to about 90 psig. In one embodiment, the target pressure is 50 psig. In one embodiment, the target pressure is 80 psig.

Once the pressure between the flow control valve 40 and the check valve 58 has reached its target pressure, the compressed medium supply 50 should be shut off and the pressure within the fuel supply system 22 should be monitored to detect any leaks other than a tube fitting leak downstream of the vent port 48. For example, a decrease in pressure reading at the pressure sensor 44 may indicate a faulty check valve 58, a faulty fluid coupling or other leak within the fuel supply system 22. If a leak is detected at this point, the fuel supply system 22 may be depressurized and the leak fixed. The fuel supply system 22 may then be re-pressurized and monitored to ensure the leak has been fixed. If the pressure continues to drop, the previous steps may be repeated until the pressure reading within the fuel supply system is stabilized. "Stabilized" as used herein may refer to a condition where the pressure in the system does not change more than about 10 psig per minute.

At step 106, method 100 includes tracing and/or detecting leaks along the various tubes and/or fluid couplings of the fuel supply system and/or along one or more of the fuel circuits 56 between the fuel distribution manifold 46 and the corresponding check valve 58 using an ultrasonic detection device 66 such as Ultraprobe® 9000 provided by UE Systems Inc., Elmsford, N.Y., U.S.A. As an operator approaches each tube fitting 60 or fluid connection/coupling, the ultrasonic device should be running, thereby allowing the operator to be able to listen for leaks along the tubing runs and to determine the presence of leaks in the tubing/fitting 60. In addition, the operator will be able to define an ambient noise baseline, and a discernable, step-change in sound from the baseline will occur when encountering a fitting leak or other leak relative to the ambient background noise. In other embodiments, there are shielding/isolation techniques that can be used to reduce competing ultrasound noise, thus helping to increase detection capability and isolating locations of leaks.

At each tube fitting 60, the operator may attempt to turn a related connection nut (not shown) of the tube fitting 60 to ensure that is has not been left finger tight. At the connection, the operator may aim or point a receiver portion 68 of the ultrasonic detection device 66 at the tube fitting 60 and listen around the entire circumference of the tube fitting 60, both upstream and downstream of the connection nut. If the connection is a union or tee, this will be done for all two or three connections, respectively. In particular embodiments, the operator may spray an air leak detection liquid or "Liquid Leak Amplifier" (LLA) such as a rapidly vaporizing liquid (i.e. alcohol) on one or more of the tube fittings 60. Bubbling of the liquid and/or 'popping' sounds detected by the ultrasonic device will be indicative of a leak. If you use LLA or some enhancement material detectable db levels may not necessarily increase. As a result, a second mode of detection with bubbles popping may be used. In one embodiment, the liquid leak amplifier may be used in addition to or as an alternative to applying the leak detection liquid. The liquid leak amplifier is a fluid that is specifically engineered to have a high surface tension such that is makes a distinct "cracking" sound when the bubbles burst. The bubbles generated are very small unlike the bubbles generated by a soap/water mixture commonly referred to as "Snoop".

It should be noted that, in some alternative implementations, the functions noted in the steps may occur out of the order noted in the figures or described herein. For example, two steps shown in succession may, in fact, be executed substantially concurrently, or the steps may sometimes be executed in the reverse order, depending upon the functionality involved. Although specific embodiments have been illustrated and described herein, it should be appreciated that any arrangement, which is calculated to achieve the same purpose, may be substituted for the specific embodiments shown and that the invention has other applications in other environments. This application is intended to cover any adaptations or variations of the present invention. The following claims are in no way intended to limit the scope of the invention to the specific embodiments described herein.

What is claimed:

1. A method for detecting leakage at a liquid fluid connection for a gas turbine fuel supply system, comprising:
   shutting off fuel flow to the fuel supply system with a flow control valve;

pressurizing the fuel supply system from a downstream side of the flow control valve to an upstream side of a check valve with a compressed medium via a compressed medium supply to a target pressure, wherein the target pressure is less than a pressure threshold of the check valve such that, the check valve does not open, the check valve disposed downstream from the compressed medium supply and upstream from a corresponding combustor of the gas turbine, and aiming a receiver portion of an ultrasonic detection device proximate to at least one tube fitting or fluid coupling of the fuel supply system between the flow control valve and the combustor, wherein detection of an increase in sound level or a popping sound at the tube fitting is indicative of a leak at the tube fitting or fluid coupling.

2. The method as in claim 1, wherein the fuel supply system is pressurized with the compressed medium to a target pressure that is within a range of about 40 psig to about 90 psig.

3. The method as in claim 1, wherein the fuel supply system is pressurized with the compressed medium to a target pressure that is 50 psig.

4. The method as in claim 1, wherein the fuel supply system is pressurized with the compressed medium to a target pressure that is 80 psig.

5. The method as in claim 1, wherein the threshold pressure is within a range of about 100 psig to about 130 psig.

6. The method as in claim 1, wherein the threshold pressure is 100 psig.

7. The method as in claim 1, wherein the threshold pressure is 120 psig.

8. The method as in claim 1, further comprising monitoring for a decrease in pressure from the fuel supply system via a pressure sensor after pressurizing.

9. The method as in claim 1, further comprising applying an air leak detection liquid on one or more of tube fittings.

10. The method as in claim 9, further comprising detecting bubbling of the leak detection liquid via the ultrasonic detection device.

11. The method as in claim 1, further comprising detecting leakage at the tube fitting via a liquid leak amplifier.

12. A method of testing a fuel supply system of a gas turbine, comprising:

isolating the fuel supply system from a liquid fuel source with a flow control valve positioned upstream of a compressed gas supply;

pressurizing the fuel supply system from a downstream side of the flow control valve to an upstream side of a check valve with a compressed gas from the compressed gas supply to a target pressure, wherein the target pressure is less than an opening pressure of the check valve, whereby the check valve does not open at the target pressure, the check valve disposed downstream from the compressed gas supply and upstream from a combustor of the gas turbine;

aiming a receiver portion of an ultrasonic detection device proximate to at least one fluid coupling of the fuel supply system between the flow control valve and the combustor, wherein detection of an increase in sound level or a popping sound at the fluid coupling is indicative of a leak at the fluid coupling and wherein not detecting the increase in sound level or the popping sound at the fluid coupling while the fuel supply system is pressurized with the compressed gas at the target pressure indicates that the fluid coupling is liquid-tight with respect to a liquid fuel flowing through the fuel supply system from the liquid fuel source at a working pressure, the working pressure greater than the opening pressure of the check valve.

13. The method of claim 12, wherein the working pressure is about 500 psig and the target pressure is about 80 psig.

* * * * *